(12) United States Patent
Bartos et al.

(10) Patent No.: US 10,399,921 B2
(45) Date of Patent: Sep. 3, 2019

(54) PURIFIED TEREPHTHALIC ACID (PTA) VENT DRYER VAPOR EFFLUENT TREATMENT

(71) Applicant: BP Corporation North America Inc., Houston, TX (US)

(72) Inventors: Thomas Bartos, Arden, NC (US); Allen Nelson, Houston, TX (US); Anders Larsen-Bitsch, Wheaton, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/823,904

(22) Filed: Nov. 28, 2017

(65) Prior Publication Data

US 2018/0186718 A1     Jul. 5, 2018

Related U.S. Application Data

(60) Provisional application No. 62/440,213, filed on Dec. 29, 2016.

(51) Int. Cl.
| | |
|---|---|
| *C07C 51/487* | (2006.01) |
| *B01D 5/00* | (2006.01) |
| *B01D 53/26* | (2006.01) |
| *B01D 53/73* | (2006.01) |
| *B01D 61/02* | (2006.01) |

(Continued)

(52) U.S. Cl.
CPC ............ *C07C 51/487* (2013.01); *B01D 5/009* (2013.01); *B01D 5/0075* (2013.01); *B01D 53/26* (2013.01); *B01D 53/72* (2013.01); *B01D 53/73* (2013.01); *B01D 61/025* (2013.01); *B01L 3/00* (2013.01); *C07C 51/16* (2013.01); *C07C 51/42* (2013.01); *C07C 51/43* (2013.01); *C07C 63/26* (2013.01); *B01D 2252/103* (2013.01);

(Continued)

(58) Field of Classification Search
CPC ....... C07C 51/36; C07C 51/43; C07C 51/487; C07C 63/14; C07C 63/15; C07C 63/24; C07C 63/26

See application file for complete search history.

(56) References Cited

U.S. PATENT DOCUMENTS

| | | | |
|---|---|---|---|
| 2,741,369 A | 5/1953 | Fest | |
| 3,639,465 A * | 2/1972 | Olsen et al. | .......... C07C 51/487 562/487 |

(Continued)

FOREIGN PATENT DOCUMENTS

| | | |
|---|---|---|
| DE | 4439147 | 5/1996 |
| EP | 1212278 | 6/2002 |
| WO | WO 2010/062315 | 6/2010 |

*Primary Examiner* — Yate' K Cutliff
(74) *Attorney, Agent, or Firm* — McDonnell Boehnen Hulbert & Berghoff LLP

(57) ABSTRACT

Processes for manufacturing a purified aromatic carboxylic acid include contacting crude aromatic carboxylic acid with hydrogen in the presence of a catalyst in a hydrogenation reactor to form a purified aromatic carboxylic acid; separating vapor effluent from the purified aromatic carboxylic acid; scrubbing the vapor effluent to form a scrubber effluent; treating the scrubber effluent vapor to form a gaseous treated scrubber effluent and a liquid treated scrubber effluent; and removing at least a portion of organic impurities from the liquid treated scrubber effluent.

17 Claims, 3 Drawing Sheets

(51) Int. Cl.
    *C07C 51/16*     (2006.01)
    *C07C 51/43*     (2006.01)
    *C07C 63/26*     (2006.01)
    *B01L 3/00*     (2006.01)
    *C07C 51/42*     (2006.01)
    *B01D 53/72*     (2006.01)

(52) U.S. Cl.
    CPC .. *B01D 2257/704* (2013.01); *B01D 2257/708* (2013.01); *B01J 2231/60* (2013.01); *Y02C 20/20* (2013.01)

(56) References Cited

U.S. PATENT DOCUMENTS

| | | | |
|---|---|---|---|
| 5,354,898 A * | 10/1994 | Schroeder | C07C 51/487 562/485 |
| 5,723,656 A | 3/1998 | Abrams | |
| 6,137,001 A * | 10/2000 | Broeker | C01B 7/093 562/413 |
| 7,807,060 B2 | 10/2010 | Schmid | |
| 7,935,844 B2 | 5/2011 | Bartos | |
| 7,935,845 B2 | 5/2011 | Bartos et al. | |
| 8,173,834 B2 | 5/2012 | Bartos | |
| 9,428,436 B2 | 8/2016 | Bartos et al. | |
| 2005/0051473 A1 | 3/2005 | Suss et al. | |
| 2012/0006745 A1 | 1/2012 | Kaley et al. | |
| 2015/0166452 A1 * | 6/2015 | Bartos | C07C 51/265 562/412 |

* cited by examiner

PURIFIED TEREPHTHALIC ACID (PTA) VENT DRYER VAPOR EFFLUENT TREATMENT

TECHNICAL FIELD

The present teachings relate generally to processes for manufacturing aromatic carboxylic acids, and in particular, to processes for purifying crude aromatic carboxylic acids.

BACKGROUND

Terephthalic acid (TA) and other aromatic carboxylic acids may be used in the manufacture of polyesters (e.g., via their reaction with ethylene glycol and/or higher alkylene glycols). Polyesters in turn may be used to make fibers, films, containers, bottles, other packaging materials, molded articles, and the like.

In commercial practice, aromatic carboxylic acids have been made by liquid phase oxidation of methyl-substituted benzene and naphthalene feedstocks in an aqueous acetic acid solvent. The positions of the methyl substituents correspond to the positions of carboxyl groups in the aromatic carboxylic acid product. Air or other sources of oxygen (e.g., typically in a gaseous state) have been used as oxidants in the presence, for example, of a bromine-promoted catalyst that contains cobalt and manganese. The oxidation is exothermic and yields aromatic carboxylic acid together with by-products, including partial or intermediate oxidation products of the aromatic feedstock, and acetic acid reaction products (e.g., methanol, methyl acetate, and methyl bromide). Water is also generated as a by-product.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids having reduced levels of impurities may be made by further oxidizing crude products from liquid phase oxidation as described above at one or more progressively lower temperatures and oxygen levels. In addition, partial oxidation products may be recovered during crystallization and converted into the desired acid product.

Pure forms of terephthalic acid and other aromatic carboxylic acids having reduced amounts of impurities—for example, purified terephthalic acid (PTA)—have been made by catalytically hydrogenating less pure forms of the acids or so-called medium purity products in solution using a noble metal catalyst. In commercial practice, liquid phase oxidation of alkyl aromatic feed materials to crude aromatic carboxylic acid, and purification of the crude product, are oftentimes conducted in continuous integrated processes in which crude product from the liquid phase oxidation is used as a starting material for the purification.

In conventional PTA processes, the drying gas from the PTA dryer is passed through a water scrubber to remove solids before discharging the gas to the atmosphere. This is acceptable due to very low concentrations of volatile organic compounds (VOCs) in conventional processes. However, in more modern processes that directly couple oxidation and purification sections and/or use overhead water, higher levels of VOCs are introduced. Examples of VOCs include acetic acid, methyl acetate, and methanol. In order to meet environmental regulations, it is necessary to further treat the drying gas before discharging it to the atmosphere.

SUMMARY

The scope of the present invention is defined solely by the appended claims, and is not affected to any degree by the statements within this summary.

According to one aspect of the invention, a process for manufacturing a purified aromatic carboxylic acid is provided. The process comprises contacting crude aromatic carboxylic acid with hydrogen in the presence of a catalyst in a hydrogenation reactor to form a purified aromatic carboxylic acid; separating a vapor effluent from the purified aromatic carboxylic acid; scrubbing the vapor effluent to form a scrubber effluent; treating the scrubber effluent to form a gaseous treated scrubber effluent and a liquid treated scrubber effluent; and removing at least a portion of organic impurities from the liquid treated scrubber effluent to form a waste steam.

According to another aspect of the invention, an apparatus for manufacturing a purified aromatic carboxylic acid is provided. The apparatus comprises a hydrogenation reactor configured for contacting crude aromatic carboxylic acid with hydrogen in the presence of a catalyst to form a purified aromatic carboxylic acid; a drying zone configured for separation of a vapor effluent from the purified aromatic carboxylic acid; a scrubbing zone configured for scrubbing the vapor effluent to form a scrubber effluent; a treatment zone configured for treating the scrubber effluent to form a liquid treated scrubber effluent and a gaseous treated scrubber effluent; and a removal zone configured for removing at least a portion of organic impurities are removed from the liquid treated scrubber effluent.

Other aspects of the invention will be apparent to those skilled in the art in view of the description that follows.

DETAILED DESCRIPTION

Figure 1:
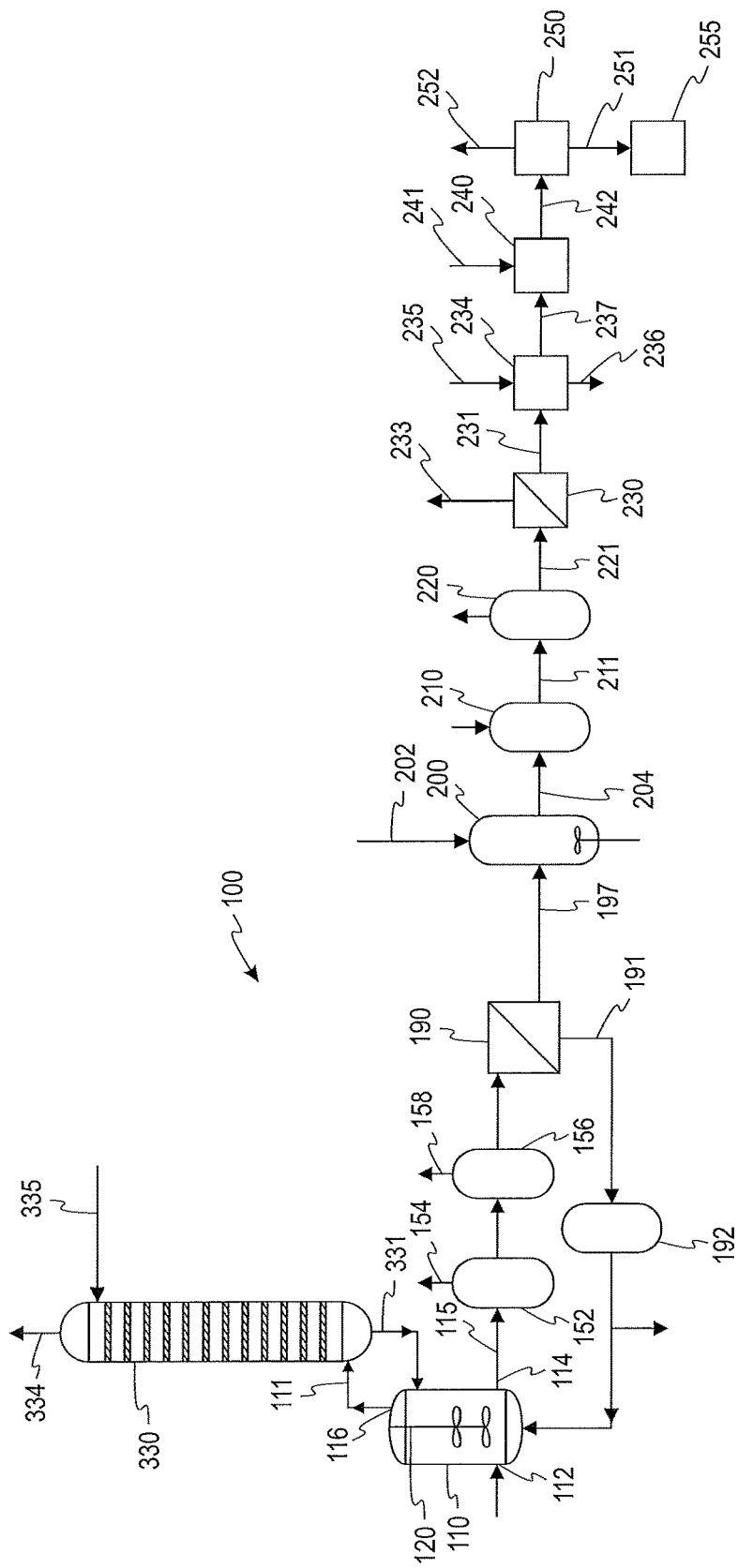
FIG. 1 shows a process flow diagram for manufacturing purified forms of aromatic carboxylic acids in accordance with the present teachings.

By way of general introduction, a process for manufacturing a purified aromatic carboxylic acid in accordance with the present invention comprises: contacting crude aromatic carboxylic acid with hydrogen in the presence of a catalyst in a hydrogenation reactor to form a purified aromatic carboxylic acid; separating vapor effluent from the purified aromatic carboxylic acid; scrubbing the vapor effluent to form a scrubber effluent; treating the scrubber effluent vapor to form a liquid treated scrubber effluent and a gaseous treated scrubber effluent; and removing at least a portion of organic impurities from the liquid treated scrubber effluent. In some embodiments, the removing step comprises recovering and/or or decomposing the at least a portion of organic impurities from the liquid treated scrubber effluent. Treatment of the scrubber effluent reduces the amount of VOCs discharged to the atmosphere, thus meeting requirements for removal of non-methane hydrocarbons.

In some embodiments, the process further comprises oxidizing a substituted aromatic compound in a reaction zone to form the crude aromatic carboxylic acid.

In some embodiments, the process further comprises crystallizing the purified aromatic carboxylic acid in a crystallization zone to form a slurry stream comprising solid purified aromatic carboxylic acid. In some embodiments, the process further comprises separating purified carboxylic acid solids from the slurry stream in a separation zone. In some embodiments, the process further comprises drying the purified carboxylic acid solids in a drying zone to form a purified carboxylic acid product and the vapor effluent.

In some embodiments, the treating step comprises condensing the scrubber effluent in at least one heat exchanger to form the liquid treated scrubber effluent and the gaseous treated scrubber effluent. In some embodiments, the treating step further comprises thermally oxidizing the gaseous treated scrubber effluent.

In some embodiments, the treating step comprises scrubbing the scrubber effluent in a caustic scrubber to form the liquid treated scrubber effluent and the gaseous treated scrubber effluent. In some embodiments, the scrubbing step and the treating step are performed in the same piece of equipment.

In some embodiments, the treating step comprises oxidizing the scrubber effluent in a thermal oxidizer to form the gaseous treated scrubber effluent, and wherein the scrubber effluent is heated prior to being oxidized.

An apparatus for manufacturing a purified aromatic carboxylic acid in accordance with the present invention comprises: a hydrogenation reactor configured for contacting crude aromatic carboxylic acid with hydrogen in the presence of a catalyst to form a purified aromatic carboxylic acid; a drying zone configured for separation of a vapor effluent from the purified aromatic carboxylic acid; a scrubbing zone configured for scrubbing the vapor effluent to form a scrubber effluent; a treatment zone configured for treating the scrubber effluent to form a liquid treated scrubber effluent and a gaseous treated scrubber effluent; and a removal zone configured for removing at least a portion of organic impurities from the liquid treated scrubber effluent.

In some embodiments, the treatment zone comprises at least one heat exchanger configured for condensing the scrubber effluent. In some embodiments, the treatment zone comprises a second scrubbing zone configured for scrubbing the scrubber effluent. In some embodiments, the scrubbing zone and the treatment zone are combined into a single zone. In some embodiments, the treatment zone comprises a thermal oxidation zone configured for oxidizing the scrubber effluent. In some embodiments, the removal zone comprises a waste water treatment zone configured for decomposing the at least a portion of organic impurities and/or a reverse osmosis apparatus configured for recovering the at least a portion of organic impurities.

Additional features of the above-described processes for manufacturing purified forms of aromatic carboxylic acid in accordance with the present teachings will now be described, in reference to the drawing figures.

FIG. 1 shows a process flow diagram for manufacturing purified forms of aromatic carboxylic acids in accordance with one embodiment of the present invention. As a brief introduction, the process 100 includes a reaction zone comprising an oxidation reactor 110 configured for liquid phase oxidation of feedstock; a crystallization zone configured for forming crude aromatic carboxylic acid from the liquid phase oxidation reaction mixture, and comprising crystallization vessels 152 and 156; a solid-liquid separation device 190 configured for separating crude aromatic carboxylic acid (and oxidation by-products) from liquid, a mixing zone including a purification reaction mixture make up vessel 200 configured for preparing mixtures of crude aromatic carboxylic acid in purification reaction solvent; a purification zone including a hydrogenation reactor 210 configured for contacting the crude aromatic carboxylic acid with hydrogen in the presence of a catalyst to form a purified aromatic carboxylic acid; and a recovery zone comprising a crystallization zone including vessel 220 configured for forming a slurry stream comprising solid purified aromatic carboxylic acid and a vapor stream, wherein the vapor stream comprises steam and hydrogen; a solid-liquid separation device 230 configured for separating purified solid product from liquid; a drying zone 234 be configured for separation of a vapor effluent from the purified solid product; a scrubbing zone 240 configured for scrubbing the vapor effluent to form a scrubber effluent; a treatment zone 250 configured for treating the scrubber effluent to form a liquid treated scrubber effluent and a gaseous treated scrubber effluent; and a removal zone 255 configured for removing at least a portion of organic impurities from the liquid treated scrubber effluent.

The integration of processes in FIG. 1 is meant to be purely representative, and various other integrated, and non-integrated configurations may likewise be used.

Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams or compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

Representative aromatic feedstock materials suitable for use in the oxidation reactor 110 include but are not limited to aromatic compounds (e.g., hydrocarbons) substituted at one or more positions with at least one group that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as a hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methyl benzene, 1-hydroxymethyl-4-methylbenzene; methylacetophenone; 1,2,4-trimethylbenzene; 1-formyl-2,4-dimethyl-benzene; 1,2,4,5-tetramethyl-benzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present teachings are not restricted and include but are not limited to mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) aromatic rings that, in some embodiments, are fused (e.g., naphthalene, anthracene, etc.) and, in other embodiments, are not. In some embodiments, the aromatic carboxylic acid comprises only one carboxylic acid (e.g., —$CO_2H$) moiety or a salt thereof (e.g., —$CO_2X$, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be conducted in the oxidation reactor 110 is a liquid phase oxidation that comprises contacting oxygen gas and a feed material comprising an aromatic hydrocarbon having substituents oxidizable to carboxylic acid groups in a liquid phase reaction mixture. In some embodiments, the liquid phase reaction mixture comprises a monocarboxylic acid solvent and water in the presence of a catalyst composition comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in one or more reactors.

In a representative embodiment, such as may be implemented as shown in FIG. 1, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air may be continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reactor 110, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead gaseous stream that comprises vaporized acetic acid, water vapor, gaseous by-products from the oxidation reaction, carbon oxides, nitrogen from the air charged to the reaction, unreacted oxygen, and the like, and combinations thereof.

In some embodiments, liquid effluent comprising solid oxidation products slurried in the liquid phase reaction mixture is removed from reaction vessel 110 through slurry outlet 114 and directed in stream 115 to crystallization vessel 152, and in turn crystallization vessel 156, for recovery of a solid product.

The gaseous stream may be removed from the reactor through vent 116 and sent in a stream 111 to a distillation column 330. The distillation column 300 is configured to separate water from the solvent monocarboxylic acid and return a solvent-rich liquid phase to the reactor in line 331. A distilled gaseous stream is removed from the distillation column 330 in line 334 and for further processed. Reflux is returned to the distillation column 330 in line 335. The reflux fluid may include condensed portions of the water rich gas stream 334 or may include fluid from other sources. Examples of further processing of the overhead gas stream and sources of reflux fluids are more fully described in U.S. Pat. Nos. 5,723,656, 6,137,001, 7,935,844, 7,935,845, and 8,173,834.

In some embodiments, solid crude product may be recovered from the liquid by crystallization in one or more stages, such as in a single crystallization vessel or, as shown in FIG. 1, in a series of multiple stirred crystallization vessels. In some embodiments, the crystallization process comprises sequential reductions in temperature and pressure from earlier to later stages to increase product recovery. By way of example, as shown in FIG. 1, crystallization vessels 152 and 156 may be provided in series and in fluid communication, such that product slurry from vessel 152 may be transferred to vessel 156. Cooling in the crystallization vessels may be accomplished by pressure release. One or more of the crystallization vessels may be vented, as at vents 154 and 158, to remove vapor resulting from pressure let down and generation of steam from the flashed vapor to a heat exchange means (not shown).

As shown in FIG. 1, the crystallization vessel 156 is in fluid communication with a solid-liquid separation device 190. The solid-liquid separation device 190 is configured to receive a slurry of solid product from the crystallization vessel 156. In some embodiments, the solid-liquid separation device 190 is further configured to separate a crude solid product and by-products from the liquid. In some embodiments, the separation device 190 is a centrifuge, a rotary vacuum filter, a pressure filter, or the like, or a combination thereof. In some embodiments, the separation device 190 comprises a pressure filter configured for solvent exchange (e.g., by positive displacement under pressure of mother liquor in a filter cake with wash liquid comprising water). Suitable rotary pressure filters are sold by BHS-Sonthofen and are disclosed for example, in U.S. Pat. Nos. 2,741,369 and 7,807,060, and United States Patent Application Publication No. 2005/0051473. The oxidation mother liquor resulting from the separation may exit separation device 190 in stream 191 for transfer to mother liquor drum 192. A portion of the mother liquor and, in some embodiments, a major portion of the mother liquor, may be transferred from drum 192 to oxidation reactor 110. In such a way, monocarboxylic acid solvent, water, catalyst, and/or oxidation reaction by-products dissolved and/or present as fine solid particles in the mother liquor may be returned to the liquid phase oxidation reaction.

As shown in FIG. 1, the stream 197 comprising heated crude solid product may be directed to a mixing zone including a reaction mixture make up vessel 200. The crude solid product in stream 197 may be mixed and slurried in make-up vessel 200 in with a make-up solvent entering vessel 200 through line 202 to form a purification reaction mixture comprising crude aromatic carboxylic acid. The purification reaction mixture prepared in vessel 200 is withdrawn through line 204. In some embodiments, the purification make-up solvent contains water. In some embodiments, the solvent line 202 connects to a holding vessel (not shown) for containing make-up solvent. In other embodiments, the solvent comprises fresh demineralized water fed from a deaerator. In other embodiments, the solvent is supplied from another part of the integrated process 100. For example, in one embodiment, the solvent comprises the condensate obtained from an off-gas separation in column 330 or from vapors recovered from a crystallization zone Sources of purification make-up solvent are more fully described, for example, in U.S. Pat. Nos. 5,723,656, 6,137,001, 7,935,844, 7,935,845, and 8,173,834. Suitable sources of purification make-up solvent include demineralized water, steam condensate, condensate from distillation in the oxidation section, such as overhead condensed from stream 334, and condensate from purification crystallizers such as 220. As discussed, the make-up solvent may include unwanted VOCs that need to be removed.

Purification reaction mixture exiting vessel 200 through line 204 enters a purification zone. The purification zone includes a purification reactor 210. In some embodiments, the purification reactor 210 is a hydrogenation reactor and purification in the purification reactor 210 comprises contacting the purification reaction mixture comprising crude aromatic carboxylic acid with hydrogen in the presence of a hydrogenation catalyst. In some embodiments, a portion of the purification liquid reaction mixture may be continuously removed from hydrogenation reactor 210 in stream 211 and directed to a crystallization vessel 220 in a downstream crystallization zone. In some embodiments, in crystallization vessel 220, terephthalic acid and reduced levels of impurities may be crystallized from the reaction mixture. The resulting slurry stream comprising solid purified aromatic carboxylic acid and liquid formed in vessel 220 may be directed to solid-liquid separation device 230 in stream 221. Purified carboxylic acid exits solid-liquid separation device 230 in the stream 231. In some embodiments, at least a portion, in some embodiments all or substantially all, of a purification mother liquor may be directed in stream 233 as reflux to high-pressure distillation column 330, as more fully described, for example, in U.S. Pat. Nos. 5,723,656, 6,137,001, 7,935,844, 7,935,845, and 8,173,834. In other embodiments, stream 233 may be directed to a waste water treatment facility. The solid-liquid separation device 230 may be a centrifuge, a rotary vacuum filter, a pressure filter, or the like, or a combination thereof.

In some embodiments, the purified carboxylic acid enters a drying zone 234 through stream 231. Drying zone 234 may be configured for separation of a vapor effluent from the purified aromatic carboxylic acid. An inert gas may enter the drying zone 234 through stream 235. The purified carboxylic acid may exit the apparatus through stream 236. The vapor effluent may be directed to a scrubbing zone 240 through stream 237.

The scrubbing zone 240 may be configured to scrub the vapor effluent in stream 237 to form a scrubber effluent. A scrubbing fluid may enter the scrubbing zone 240 through stream 241. In some embodiments, the scrubbing fluid may be deionized water. In some embodiments, the scrubbing fluid may be a caustic fluid. The scrubber effluent may be directed to a treatment zone 250 through stream 242.

The treatment zone 250 may be configured to treat the scrubber effluent to form a liquid treated scrubber effluent and a gaseous treated scrubber effluent. VOCs may be removed from the scrubber effluent in the treatment zone 250. The scrubber effluent may comprise more than about 5 percent non-methane hydrocarbons on a dry basis. The gaseous treated scrubber effluent may comprise less than about 5 percent non-methane hydrocarbons on a dry basis. The liquid treated scrubber effluent may be directed through stream 251 to a removal zone 255. The removal zone 255 may be a waste water treatment zone and may include anaerobic and aerobic reactors. In some embodiments, the waste water treatment zone may include an upflow blanket reactor followed by an aerobic reactor, as shown in United States Patent Application Publication No. 2012/0006745. In some embodiments, the removal zone 255 may be a reverse osmosis apparatus. In some embodiments, the removal zone 255 may comprise a waste water treatment zone and a reverse osmosis apparatus. The gaseous treated scrubber effluent may be directed through stream 252 to the atmosphere or to a thermal oxidation reactor. Organic impurities may be removed from the liquid treated scrubber effluent in the removal zone 255. Examples of organic impurities include acetic acid and methyl acetate. The removal step may comprise recovering and/or decomposing at least a portion of the organic impurities. In some embodiments, the organic impurities in the liquid treated scrubber effluent may be decomposed in a waste water treatment zone. In some embodiments, the organic impurities may be recovered from the liquid treated scrubber effluent through reverse osmosis.

Figure 2:
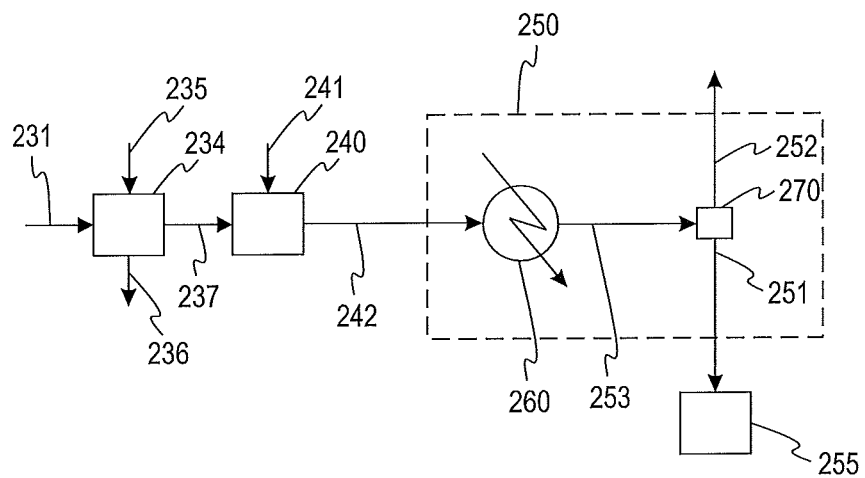
FIG. 2 shows a process flow diagram for treating dryer gas in accordance with the present teachings.
Figure 3:
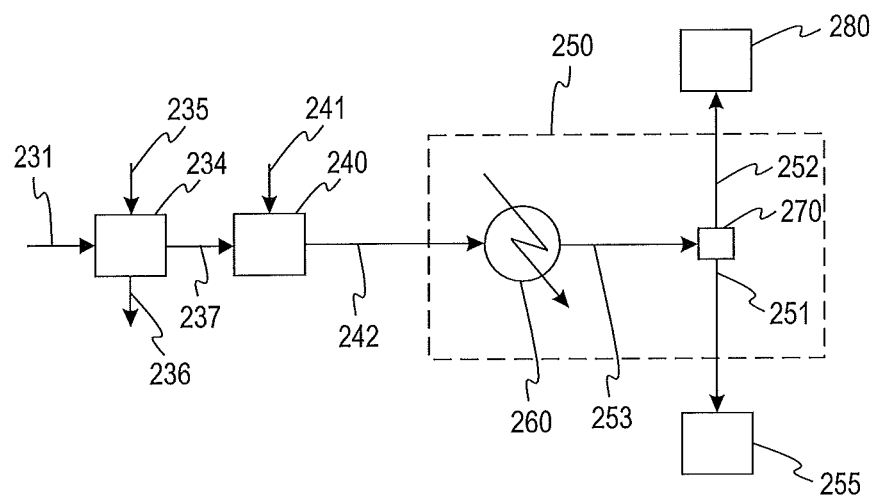
FIG. 3 shows a process flow diagram for treating dryer gas in accordance with the present teachings.

In some embodiments, the treatment zone 250 comprises at least one heat exchanger 260 configured to condense the scrubber effluent using a cooling medium and a separation vessel 270 configured to separate the two-phase flow in stream 253 leaving the heat exchanger 260 into the liquid treated scrubber effluent 251 and the gaseous treated scrubber effluent 252, as shown in FIG. 2. The cooling medium may be water or any other process stream that needs to be heated up to about 98° C. The scrubber effluent may enter the at least one heat exchanger 260 at a temperature about 95-102° C. The liquid treated scrubber effluent may exit the at least one heat exchanger 260 at a temperature of about 30-80° C. The temperature of the treated scrubber effluent exiting the at least one heat exchanger 260 may depend on cooling medium temperature and heat exchanger size. The liquid treated scrubber effluent 251 may be directed to a waste water treatment system for decomposition of organic impurities. The gaseous treated scrubber effluent 252 may be directed to the atmosphere. In some embodiments, the gaseous treated scrubber effluent 252 may be directed to a thermal oxidation zone 280 for further removal of VOCs, as shown in FIG. 3.

Figure 4:
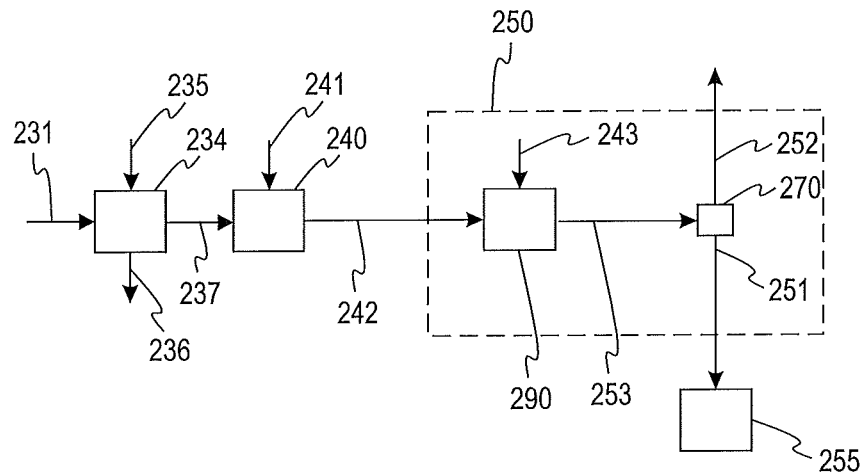
FIG. 4 shows a process flow diagram for treating dryer gas in accordance with the present teachings.

In some embodiments, the treating step comprises scrubbing the scrubber effluent with a caustic substance. In this embodiment, treatment zone 250 comprises a second scrubbing zone 290, as shown in FIG. 4. The second scrubbing zone 290 may comprise a caustic scrubber and the caustic substance may be added to the second scrubbing zone 290 through line 243. In some embodiments, the treating step further comprises cooling the gaseous treated scrubber effluent and thermally oxidizing the gaseous treated scrubber effluent.

Figure 5:
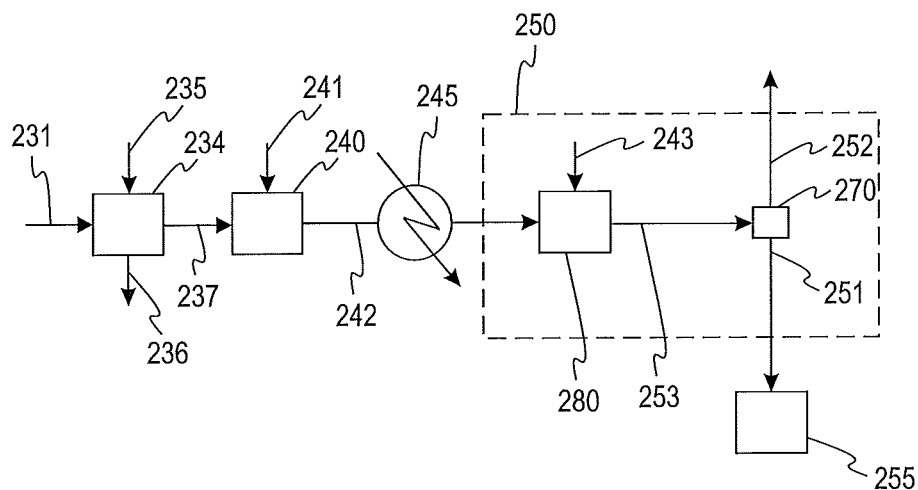
FIG. 5 shows a process flow diagram for treating dryer gas in accordance with the present teachings.

In some embodiments, the treatment zone 250 comprises a thermal oxidation zone 280, as shown in FIG. 5. Stream 242 may be heated prior to entry in the thermal oxidation zone 280. Stream 242 may be heated by methods known in the art, such as heat exchangers (for example, heat exchanger 245) or electric heaters. The thermal oxidation zone 280 may comprise a catalytic oxidation reactor. In some embodiments, the thermal oxidation zone 280 performs the entire treating step. In some embodiments, the thermal oxidation zone 280 is used after another treating step, such as condensing, as illustrated in FIG. 3. Thermal oxidation may be performed without removing water from stream 242. In some embodiments, water is removed from stream 242 prior to thermal oxidation in order to save energy. In some embodiments, a blower or a pump may be used to overcome a pressure drop downstream of drying zone 234.

In some embodiments, the at least one heat exchanger 260, the thermal oxidation zone 280, and/or the second scrubbing zone 290 may be used alone or in series.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

EXAMPLES

Example 1: Condensing the Scrubber Effluent

The scrubber effluent is condensed in one more heat exchangers which are either used for heat recovery and/or using cooling water. The cooling medium may be water, or any other process stream that needs to be heated from low temperature up to about 98° C. Outlet temperature can be optimized based on the composition of the stream leaving the vent scrubber and local regulations.

TABLE 1

Reduction in organic components from treating the vent stream by cooling.

| wt % dry | Leaving Vent | Leaving Condenser(s) | Reduction |
| --- | --- | --- | --- |
| Nitrogen/CO2/O2 | Balance | Balance | 0% |
| Methyl Acetate | 0.1% | 0.03% | 66% |
| Methanol | 0.1% | 0.00% | 97% |
| Acetic Acid | 8.90% | 0.02% | 100% |
| Temperature C. | 100 | 40 | |

As shown in Table 1, VOCs such as methyl acetate, methanol, and acetic acid are reduced by treatment of the scrubber effluent by cooling. Other components such as aromatic acids will, if present, be reduced in excess of 99%.

Example 2: Caustic Scrubbing

Traces of acids such as acetic acid or aromatic acids can be effectively removed using a caustic scrubber, such as those known in the art. The caustic scrubbing can be combined with deionized water scrubbing in one piece of equipment for reduced equipment count.

TABLE 2

Reduction in organic components from treating the vent stream by caustic scrubbing.

| Dry Basis | Leaving Vent Scrubber | Leaving Caustic Scrubber | Reduction |
| --- | --- | --- | --- |
| N2/CO2/O2 | Balance | Balance | |
| Methyl Acetate | 0.1% | 0.1% | 1% |
| Methanol | 0.1% | 0.1% | 5% |
| Acetic Acid | 8.9% | 0.0% | 100% |

Example 3: Thermal Oxidation

Thermal oxidation, such as catalytic oxidation, can be employed in series as a final step or on the entire stream without removing the majority of the water present. A majority of water in the scrubber effluent may be removed prior to oxidizing the organic components for energy saving purposes. In order to avoid pressuring up the drying zone upstream, a blower or pump may be used to overcome downstream pressure drop.

The oxygen needed for the oxidation reaction is either present in the scrubber effluent (when oxygen is used in the drying zone as sweep gas) or can be added prior to catalytic oxidation. A convenient source of oxygen is exhaust gas from catalytic oxidation processes elsewhere in the PTA process. The stream is heated prior the oxidation reaction to obtain good conversion. The heat source can be direct or indirect via heat exchange use of steam low (<10 bar) or high (>=10 bar) or a combination, hot oil, furnace, or electric heater. Sacrificial fuels, for example, $H_2$, can also be added directly to the process. The conversion rates targeted for VOC's are typically greater than 98%.

TABLE 3

Reduction in organic components from thermally oxidizing the scrubber effluent.

| Component | ppmw dry | ppmw dry | Reduction |
|---|---|---|---|
| Methyl Acetate | 353 | 7 | 98% |
| Methanol | 177 | 4 | 98% |
| Acetic Acid | 212 | 4 | 98% |
| Temperature C. | 280 | 286 | |

The invention claimed is:

1. A process for manufacturing a purified aromatic carboxylic acid comprising:
   contacting crude aromatic carboxylic acid with hydrogen in the presence of a catalyst in a hydrogenation reactor to form a purified aromatic carboxylic acid;
   separating a vapor effluent from the purified aromatic carboxylic acid;
   scrubbing the vapor effluent to form a scrubber effluent;
   treating the scrubber effluent to form a gaseous treated scrubber effluent and a liquid treated scrubber effluent; and
   removing at least a portion of organic impurities from the liquid treated scrubber effluent.

2. The process of claim 1, wherein the removing step comprises recovering the at least a portion of organic impurities from the liquid treated scrubber effluent.

3. The process of claim 1, wherein the removing step comprises decomposing the at least a portion of organic impurities from the liquid treated scrubber effluent.

4. The process of claim 1, wherein the removing step comprises recovering at least a first portion of organic impurities from the liquid treated scrubber effluent and decomposing at least a second portion of organic impurities from the liquid treated scrubber effluent.

5. The process of claim 1, further comprising oxidizing a substituted aromatic compound in a reaction zone to form the crude aromatic carboxylic acid.

6. The process of claim 1, further comprising crystallizing the purified aromatic carboxylic acid in a crystallization zone to form a slurry stream comprising solid purified aromatic carboxylic acid.

7. The process of claim 6, further comprising separating purified carboxylic acid solids from the slurry stream in a separation zone.

8. The process of claim 7, wherein the separating step comprises drying the purified carboxylic acid solids in a drying zone to form a purified carboxylic acid product and the vapor effluent.

9. The process of claim 1, wherein the scrubber effluent comprises more than about 5 percent non-methane hydrocarbons on a dry basis.

10. The process of claim 1, wherein the gaseous treated scrubber effluent comprises less than about 5 percent non-methane hydrocarbons on a dry basis.

11. The process of claim 1, wherein the treating step comprises condensing the scrubber effluent in at least one heat exchanger to form the liquid treated scrubber effluent and the gaseous treated scrubber effluent.

12. The process of claim 11, wherein the scrubber effluent is at a temperature of about 95-102 degrees Celsius, and wherein the liquid treated scrubber effluent is at a temperature of about 30-80 degrees Celsius.

13. The process of claim 11, wherein the treating step further comprises thermally oxidizing the gaseous treated scrubber effluent.

14. The process of claim 1, wherein the treating step comprises scrubbing the scrubber effluent with a caustic substance to form the liquid treated scrubber effluent and the gaseous treated scrubber effluent.

15. The process of claim 14, wherein the scrubbing step and the treating step are performed in the same piece of equipment.

16. The process of claim 14, wherein the treating step further comprises cooling the gaseous treated scrubber effluent and thermally oxidizing the gaseous treated scrubber effluent.

17. The process of claim 1, wherein the treating step comprises oxidizing the scrubber effluent in a thermal oxidizer to form the gaseous treated scrubber effluent, and wherein the scrubber effluent is heated prior to being oxidized.

* * * * *